(12) United States Patent
Puci et al.

(10) Patent No.: US 10,370,326 B2
(45) Date of Patent: *Aug. 6, 2019

(54) UREA AMMONIUM NITRATE PRODUCTION COMPRISING CONDENSATION

(71) Applicant: Stamicarbon B.V., Sittard (NL)

(72) Inventors: Giusy Elisa Puci, Sittard (NL); Joey Dobree, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/573,452

(22) PCT Filed: Dec. 21, 2016

(86) PCT No.: PCT/NL2016/050905
§ 371 (c)(1),
(2) Date: Nov. 10, 2017

(87) PCT Pub. No.: WO2017/111588
PCT Pub. Date: Jun. 29, 2017

(65) Prior Publication Data
US 2018/0354895 A1    Dec. 13, 2018

(30) Foreign Application Priority Data

Dec. 21, 2015   (EP) .................................... 15201582

(51) Int. Cl.
| | | |
|---|---|---|
| C07C 273/16 | (2006.01) | |
| C07C 273/04 | (2006.01) | |
| C05C 1/00 | (2006.01) | |
| B01D 53/00 | (2006.01) | |
| B01D 53/14 | (2006.01) | |
| C01C 1/18 | (2006.01) | |

(52) U.S. Cl.
CPC .......... *C07C 273/04* (2013.01); *B01D 53/002* (2013.01); *B01D 53/1493* (2013.01); *C01C 1/185* (2013.01); *C05C 1/00* (2013.01); *C07C 273/16* (2013.01); *B01D 2251/404* (2013.01); *B01D 2251/504* (2013.01); *B01D 2252/10* (2013.01); *B01D 2257/406* (2013.01)

(58) Field of Classification Search
CPC ..................................................... C07C 273/04
See application file for complete search history.

(56) References Cited

U.S. PATENT DOCUMENTS

2015/0217221 A1    8/2015  Wang et al.

FOREIGN PATENT DOCUMENTS

| | | |
|---|---|---|
| EP | 0 514 902 | 11/1992 |
| FR | 2 296 603 | 7/1976 |
| WO | WO-2009/009725 | 1/2009 |

OTHER PUBLICATIONS

International Search Report and Written Opinion for PCT/NL2016/050905, dated Apr. 4, 2017, 9 pages.

*Primary Examiner* — Ana Z Muresan
(74) *Attorney, Agent, or Firm* — Morrison & Foerster LLP

(57) ABSTRACT

The invention relates to a process for the production of urea ammonium nitrate, a system and a method of modifying a plant. The process comprises subjecting ammonia-containing off-gas resulting from the production of ammonium nitrate (AN off-gas) to condensation under acidic conditions so as to form an acidic a acidic scrubbing liquid in a finishing treatment section having a gas inlet in fluid communication with a gas outlet of a finishing section of a urea production unit, wherein the finishing section is adapted to solidify urea liquid, and wherein said finishing treatment section is adapted to subject ammonia-containing off-gas of the finishing section to treatment with an acidic scrubbing liquid.

18 Claims, 1 Drawing Sheet

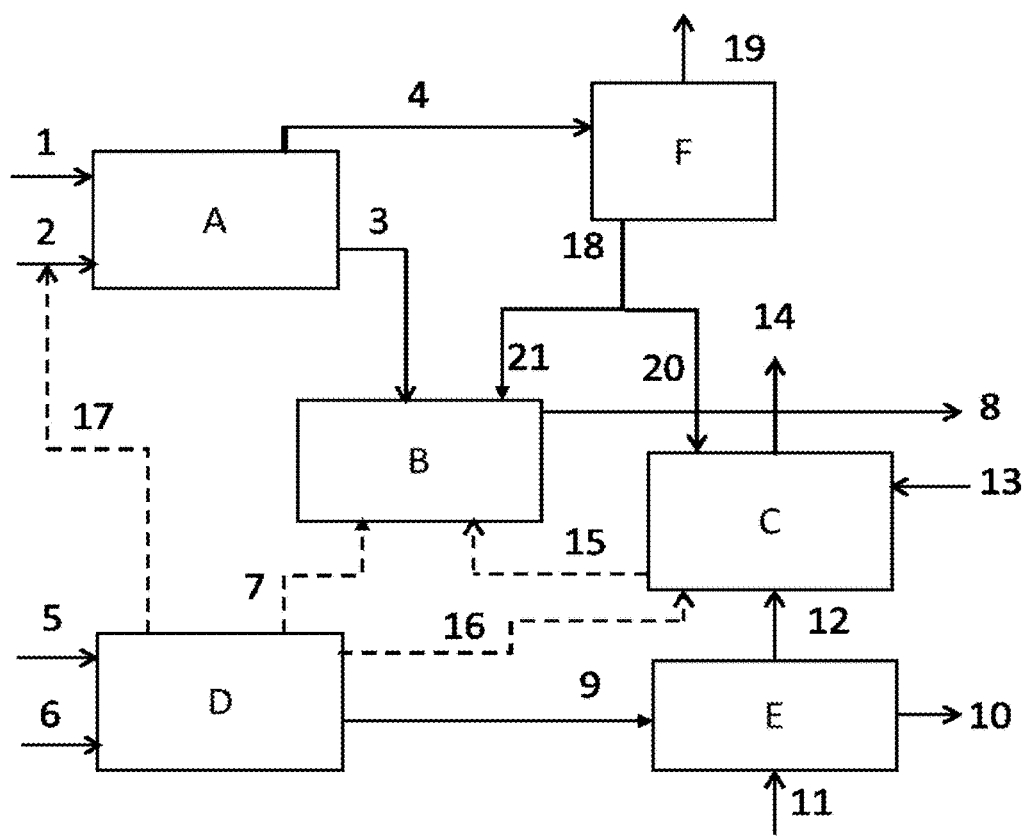

US 10,370,326 B2

UREA AMMONIUM NITRATE PRODUCTION COMPRISING CONDENSATION

CROSS-REFERENCE TO RELATED APPLICATIONS

This application is the national phase of PCT application PCT/NL2016/050905 having an international filing date of 21 Dec. 2016, which claims benefit of European patent application No. 15201582.2 filed 21 Dec. 2015. The contents of the above patent applications are incorporated by reference herein in their entirety.

FIELD OF THE INVENTION

The invention is in the field of the production of a solution of urea ammonium nitrate in water (UAN). The invention also pertains to a system for producing UAN and to a method of modifying a plant.

BACKGROUND OF THE INVENTION

Urea ammonium nitrate (UAN) is an aqueous solution of urea and ammonium nitrate and is used as fertilizer. A process for producing UAN generally comprises producing ammonium nitrate in an ammonium nitrate section (AN production section), forming urea in a urea production unit, and combining said produced ammonium nitrate and urea to produce urea ammonium nitrate in a urea ammonium nitrate section (UAN production section).

The production of ammonium nitrate solution involves the neutralisation reaction of gaseous ammonia with concentrated nitric acid solution according to the following reaction:

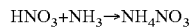

$$HNO_3 + NH_3 \rightarrow NH_4NO_3$$

The production of ammonium nitrate solution generally results in an off-gas (AN off-gas), in particular from the neutralization reaction of ammonia with nitric acid. Because the formation of ammonium nitrate is a highly exothermic reaction, the AN off-gas generally comprises water vapor, residual ammonia and entrained droplets from the reaction medium. The droplets can comprise ammonium nitrate and/or nitric acid. Accordingly, AN off-gas may for instance comprise $CO_2$, $NH_3$, water, ammonium nitrate, $N_2$, $O_2$ and nitric acid. The AN off-gas is usually subjected to condensation and the condensate is for instance passed in part to the UAN production section.

Some general desires for improving a process comprising producing UAN include reducing steam consumption (increasing energy efficiency) and reducing emissions and emission points, in particular of ammonia. It is also desired to reduce waste streams, improve product recovery and reduce the amount of make-up water and acid used for scrubbing. Such advantages are desirably obtained for new plants (grass-roots plants) as well as by modifying or revamping existing plants. Equipment costs and other capital expenditures are preferably minimized.

SUMMARY OF THE INVENTION

In the description that follows, one component of the invention is consistently labeled a "finishing treatment section". As this may cause confusion in relation to another component of the invention —the urea "finishing section" —the claims have been amended to change the name of this feature to a less confusing term, namely an "off-gas treatment section." Therefore, where the term "finishing treatment section" occurs, it should be read as an "off-gas treatment section." It will be noted that this is represented in the drawing as Item "C" and that it accepts the off-gas from the urea finishing section E, as well as the condensate from the condenser F that treats the off-gases from the ammonium nitrate section A, as is described hereinbelow.

In order to better address one or more of the foregoing desires, the invention, in one aspect, provides a process for the production of urea ammonium nitrate, comprising:

(a) subjecting ammonia and carbon dioxide to urea forming conditions so as to obtain an aqueous urea solution, (b) purifying the aqueous urea solution in a recovery section to remove residual ammonium carbamate so as to form a purified aqueous urea solution, and optionally subjecting at least part of the purified aqueous urea solution to evaporation so as to form concentrated urea liquid (urea melt), (c) subjecting ammonia and nitric acid to ammonium nitrate forming conditions so as to form an aqueous ammonium nitrate solution;

(d) combining said aqueous ammonium nitrate solution and at least a part of the purified aqueous urea solution and/or concentrated urea liquid in a urea ammonium nitrate section so as to obtain an aqueous solution of urea ammonium nitrate;

(e) subjecting ammonia-containing off-gas resulting from the production of ammonium nitrate (AN off-gas) to condensation under acidic conditions so as to form an acidic condensate, and using at least part of the acidic condensate as an acidic scrubbing liquid in a finishing treatment section having a gas inlet in fluid communication with a gas outlet of a finishing section of a urea production unit, wherein the finishing section is adapted to solidify urea liquid, and wherein said finishing treatment section is adapted to subject ammonia-containing off-gas of the finishing section to treatment with an acidic scrubbing liquid.

The invention also relates to a system for the production of at least urea and urea ammonium nitrate, preferably suitable for the process of the invention, comprising:

(a) a urea production unit comprising a finishing section, wherein the finishing section has a gas outlet for ammonia-containing off-gas, (b) an ammonium nitrate section for producing ammonium nitrate in fluid communication with a source of nitric acid and a source of ammonia, having an outlet for aqueous ammonium nitrate solution and an outlet for off-gas, and a condensation section in fluid communication with said outlet for off-gas, for condensing at least part of said off-gas to form an acidic condensate, (c) a urea ammonium nitrate section comprising a unit having an inlet in fluid connection with said outlet for aqueous ammonium nitrate solution and an inlet for receiving urea liquid, for combining said ammonium nitrate solution and said urea liquid, and having an outlet for urea ammonium nitrate solution, and (d) a finishing treatment section having a gas inlet in fluid connection with said gas outlet for off-gas of said finishing section, adapted to subject ammonia-containing off-gas of the finishing section to treatment with an acidic scrubbing liquid, wherein said finishing treatment section comprises an inlet in fluid communication with said condensation section for receiving said acidic condensate.

The invention also relates to a method of modifying a plant, wherein the plant comprises an ammonium nitrate section for reacting ammonia and nitric acid under ammonium nitrate forming conditions, a condensation section in fluid communication with said ammonium nitrate section for condensing under acidic conditions at least part of the off-gas from said ammonium nitrate section, a finishing section adapted to solidify a urea liquid, and a finishing treatment section having a gas inlet in fluid communication with a gas outlet of said finishing section, adapted to subject ammonia-containing off-gas of the finishing section to treatment with an acidic scrubbing liquid, wherein the method comprises adding a connection for fluid communication between an outlet for acidic condensate of said condensation section, and an inlet of said finishing treatment section, such as piping or tubing.

BRIEF DESCRIPTION OF THE DRAWING

The drawing shows a process scheme for a non-limiting example of a process and system according to the invention.

DETAILED DESCRIPTION OF THE INVENTION

The invention is based on the judicious insight to use a stream obtained from ammonia-containing off-gas resulting from the production of ammonium nitrate (AN off-gas) in the treatment of ammonia-containing off-gas of a urea finishing section (finishing off-gas). A urea finishing section refers to a section of a urea production unit that is adapted to solidify urea liquid.

The process of the invention comprises subjecting ammonia-containing off-gas resulting from the production of ammonium nitrate (AN off-gas), preferably essentially all of said off-gas, to condensation under acidic conditions so as to form an acidic condensate. At least part of the acidic condensate, preferably essentially all, is used as at least part of an acidic scrubbing liquid in a finishing treatment section.

AN off-gas which did not condense during the condensation step can for example be vented, typically after a scrubbing step, however optionally such gaseous AN off-gas stream is passed to the finishing treatment section.

In addition, if only a part of the AN off-gas is subjected to the condensation, another part of the AN off-gas not subjected to the condensation can for example be sent to the finishing treatment section in addition to said condensate Likewise, at least part or all of the non-condensed off-gas obtained from the condensation step is optionally also supplied to the finishing treatment section. In an optional embodiment, the non-condensed part of the AN off-gas is not supplied to the finishing treatment section. If in addition to the condensate, AN off-gas is supplied to the finishing treatment section, this off-gas can for example be combined with off-gas from the finishing section. Other off-gas streams, for instance from other sections of a urea production unit, may as well be treated in the finishing treatment section.

The condensate comprises for example mainly water (>99 wt. %) and in addition nitric acid and ammonium nitrate. The condensate is acidic and has a pH of for example in the range of 1-6, preferably in the range of 1.5 to 5, such as in the range of 2 to 4. Because of this pH, the condensate can be used as acidic scrubbing liquid for removal of ammonia. By using the acidic condensate as an acidic scrubbing liquid in a finishing treatment section, the amount of make-up water can be reduced, such as with up to 50%. Accordingly, the process preferably comprises scrubbing ammonia-containing off-gas of the finishing section with acidic scrubbing liquid obtained at least in part by the acidic condensing of the AN off-gas.

Herein, condensation under acidic conditions involves for example absence of conditions causing an increase of the pH, such as absence of a neutralization reaction. In some embodiments, the acidic conditions are any conditions wherein the condensate has a pH of 1-6, in particular upon entry of the finishing treatment section.

Optionally, a part of the condensate, such as 1-50 wt. % of the condensate, is for example supplied to the urea ammonium nitrate section (UAN section). In this way, the concentration of the UAN solution obtained in the UAN section can be adjusted.

Suitable condensers for condensing at least part of the AN off-gas include vertical and horizontal condensers, for example a shell and tube condenser, a plate and frame condenser, and a spiral type condenser. The condenser preferably uses indirect heat exchange with a cooling stream.

The finishing section is for example the finishing section of the urea production unit wherein aqueous urea solution and/or concentrated urea liquid are produced. In another embodiment, the finishing section is a finishing section of a second urea production unit from which no urea liquid is supplied to the urea ammonium nitrate section. In such case, the first urea production unit does not necessarily have a finishing section.

The aqueous urea solution, the purified aqueous urea solution and the concentrated urea liquid are some of the streams of urea liquid in the process of the invention. The term "urea liquid" can also refer to a urea-containing liquid stream of a second urea production unit.

Preferably, the process comprises recycling scrubbing liquid utilized in the finishing treatment section to the UAN production section. Preferably, the scrubbing liquid is recycled such that it is at least in part included in the aqueous solution of urea ammonium nitrate. The process may for example comprise combining scrubbing liquid utilized in the finishing treatment section with the aqueous ammonium nitrate solution, the purified aqueous urea solution and/or concentrated urea liquid.

The process comprises subjecting ammonia-containing off gas of the finishing section to a treatment with an acidic scrubbing liquid wherein at least part of the acidic condensate is used as part of the scrubbing liquid. Accordingly, various components of both the off-gas streams end up in a liquid stream (liquid recycle stream), in particular urea and ammonium nitrate. For example, the scrubbing uses a circulating urea solution as scrubbing liquid, with additional make-up water. A purge flow is obtained from the scrubber, usually with 10% -60% urea by weight, which provides the liquid recycle stream.

The process preferably comprises including at least part of the liquid recycle stream, such as all, in the UAN solution. Preferably, at least part of the liquid recycle stream, such as all, is combined with an ammonium nitrate containing stream in the UAN production section, for example in the mixing unit. Herein, the liquid recycle stream refers to the scrubbing liquid utilized in the finishing treatment section after withdrawal from that section.

This preferred embodiment advantageously avoids the need for a separate treatment of said liquid recycle stream. Moreover, this embodiment allows for recovering for instance ammonium nitrate and/or urea from off-gas, thereby allowing for a higher UAN production. This embodiment may also allow for recovering nitric acid from the acidic concentrate, thereby allowing for reduced nitric acid consumption in the AN production section. In addition, it can allow for adjusting the concentration of the UAN solution. A particular advantage of this embodiment is that urea in the finishing off-gas can optionally be recovered into UAN rather than in a urea product stream. Accordingly, the process allows for eliminating the recycling of any additives added to the urea, such as anti-caking agents and granulation aids, in particular formaldehydes, back into a urea production unit.

Recycling scrubbing liquid utilized in the finishing treatment section to the UAN production section is in particular advantageous if a part of the urea liquid is used as very pure urea product or is used for the production of such urea product. Examples of such urea products are Diesel Exhaust Fluid (DEF) and urea products which are suitable for the preparation of DEF by adding demineralized water (together referred to as DEF products). DEF is generally an aqueous urea solution with maximum 0.3 wt. % biuret and maximum 0.2 wt. % of alkalinity, in particular <0.2 wt. % ammonia, with 32.5 wt. % urea. DEF is injected in the tail gas of combustion engines to react with $NO_x$ to reduce $NO_x$ emission. Presence of contaminations in DEF is not desirable; in particular the presence of formaldehyde and other anti-caking agents is unwanted. DEF is generally produced by diluting a urea liquid, such as purified aqueous urea solution, or by dissolving urea granules with demineralized water. The urea liquid or urea granules accordingly should also have a very low level of biuret, alkalinity and other contaminations.

Accordingly, the process preferably comprises a step of preparing a urea product from a part a stream of urea liquid of the urea production unit having the finishing section, wherein the urea product is a DEF product. Preferably, the DEF product has maximum 0.3 wt. % biuret and maximum 0.2 wt. % of alkalinity, in particular <0.2 wt. % ammonia, and comprises maximum 0.10 wt. % additives, preferably less than 0.010 wt. % additives, or for example less than 0.010 wt. % formaldehyde, and at least 30 wt. % urea, based on total weight of the product. Preferably, the product is essentially free of formaldehyde. Preferably the process further comprises adding an additive to another part of said stream of urea liquid, for example an anti-caking agent such as formaldehyde. Hence, a preferred process comprises dividing a stream of urea liquid of the urea production unit having the finishing section in at least two parts, and adding an additive to one of said streams downstream of said dividing, wherein downstream is defined with respect to said stream, and preparing a DEF product from the other stream, wherein said additive is preferably formaldehyde, and wherein the stream with said additive is subjected to solidification in the finishing section, wherein the solidification is preferably granulation. In such process, the off-gas from the solidification is scrubbed in the finishing treatment section and the liquid recycle stream obtained with the scrubbing is included in the UAN product, for example supplied to the UAN production section.

Accordingly, a process for the production of a solid urea product, a DEF product and UAN preferably comprises producing UAN and a urea liquid, using a part of the urea liquid for producing a DEF product, and using another part of the urea liquid for producing a solid urea product by adding an additive, such as formaldehyde, and solidifying the urea, such as by granulating, wherein finishing off-gas is obtained. The off-gas comprises urea, ammonia and said additive. At least part of the urea is recovered from the off-gas into a recycle stream, for example by scrubbing, and at least part of said recycle stream is included in the UAN product. The process preferably does not comprise supplying the recycle stream into a stream from which the DEF product is prepared. This process can in principle be used independently of the feature of supplying acidic condensate to a finishing treatment section, although the combination is preferred.

A suitable process for DEF preparation is described in for example EP1856038A1 and comprises using a urea aqueous solution obtained directly from or after the recovery section of the urea melt plant, and diluting the urea aqueous solution with water to obtain the desired solution. In terms of the present invention, for example the purified aqueous urea solution can be diluted to prepare DEF.

The process comprises subjecting ammonia and carbon dioxide to urea forming conditions so as to obtain an aqueous urea solution.

The urea can be synthesized by any suitable method. A frequently used process for the preparation of urea according to a stripping process is the carbon dioxide stripping process as for example described in Ullmann's Encyclopedia of Industrial Chemistry, Vol. A27, 1996, pp 333-350. In this process, a high pressure synthesis section is followed by one or more recovery sections. The synthesis section comprises for example a reactor, a stripper, and a condenser. The synthesis section is operated at high pressure, such as between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed by formation of ammonium carbamate in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing ammonium carbamate, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment (for example a pool reactor). An example of this piece of equipment is described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is for example sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section.

Said vapor from said reactor can for example also be sent directly to the ammonium nitrate section for neutralization (i.e. reaction with nitric acid so as to form ammonium nitrate). The urea solution leaving the stripper in this synthesis section can for example have a urea concentration of at least 45% by weight and preferably at least 50% by weight thereby allowing for treatment in a single recovery system downstream the stripper. This urea solution is referred to as aqueous urea solution. These preferences also apply for the second urea production unit, if used.

In the process of the invention, at least part of the aqueous urea solution is purified in a recovery section. In this section, aqueous urea solution is purified to remove residual ammonium carbamate so as to form a purified aqueous urea solution. The recovery section comprises for example a heater, a liquid/gas separator and a condenser. The pressure in this recovery section is for instance between 200 to 6000 kPa. For example, a low pressure recovery section (2-7 bar) can be used, or a medium pressure recovery section (12-40 bar) followed by a low pressure recovery section. In the heater of the recovery section the bulk of ammonia and carbon dioxide is separated from the urea and water phase by heating the urea solution. Usually steam is used as heating agent. The purified aqueous urea solution contains a small amount of dissolved ammonia and carbon dioxide and leaves the recovery section. Optionally, at least part of the purified aqueous urea solution is sent to a downstream urea processing section, also referred to as urea evaporation section or evaporation section. Herein, purified aqueous urea solution is optionally subjected to evaporation of water so as to form a concentrated urea liquid that is generally referred to as a urea melt.

The invention is not limited to any particular urea production process. Other processes and plants include those that are based on technology such as total recycle plants, the HEC process developed by Urea Casale, the ACES process developed by Toyo Engineering Corporation and the process developed by Snamprogetti. All of these processes, and others, may be used in the process of the invention.

The process of the invention comprises subjecting ammonia and nitric acid to ammonium nitrate forming conditions so as to form an aqueous ammonium nitrate solution. This step also results in an off-gas. The unit, reactor or section in which this reaction is carried out, can be referred to as AN production section.

Ammonium nitrate can for example be produced by reacting ammonia with a strong solution of nitric acid while maintaining the pH of the solution within narrow boundaries Ammonia is for example used in its anhydrous form as gas and the nitric acid is for example concentrated (typical concentration range: 40 to 80 wt. %, such as about 60 wt. %). Via an exothermic neutralization reaction, the ammonium nitrate solution is readily formed, typically at a concentration of about 70% to 95%, such as 83% to 88%, for example with pH of about 7.

The AN production section can for instance comprise a neutralizer reactor based on a U-type combination of a circulator tube and mixing tube with a separation vessel reactor. The reaction is for example performed at 0.15 MPa and 135-165° C.

Optionally, the process may comprise preparing solid ammonium nitrate products from a part of the ammonium nitrate, such as prills or granules, wherein preferably the excess water is evaporated to an ammonium nitrate (AN) content of 95% to 99.9% concentration.

Nitric acid used in the production of ammonium nitrate can be obtained as an external feed. Preferably, the nitric acid is produced on site. Accordingly, the process optionally comprises oxidizing anhydrous ammonia to nitric oxide, for example in the presence of a catalyst, and reacting nitric oxide with oxygen to form nitrogen dioxide. The process optionally comprises absorbing nitrogen dioxide in water to form nitric acid and nitric oxide, or reacting nitrogen dioxide with oxygen and water to form nitric acid. Accordingly, the system for the process of the invention optionally comprises a unit for the production of nitric acid. This unit will generally be fed from external sources and has an outlet for nitric acid that is in fluid communication with an inlet for nitric acid of the unit for the production of ammonium nitrate.

Ammonia used in the AN production section can for example at least in part be obtained from off-gas of the urea production unit and/or from the UAN production section. Preferably, also ammonia-containing off-gas from the urea production unit and/or from the urea ammonium nitrate section is sent to a gas inlet of the finishing treatment section.

Accordingly, the process may comprise supplying to the AN production section ammonia containing off-gas, such as overhead vapors, from the urea synthesis section, the recovery section, and/or the urea evaporation section.

The off-gas may for instance be obtained from a recovery section of the urea production unit, wherein ammonium carbamate in the urea synthesis solution is decomposed to carbon dioxide and ammonia, typically at low pressure (0.1-1 MPa, in particular 0.2-0.7 MPa), and/or at medium pressure (1-4 MPa, preferably 1.5-3.0 MPa).

The process optionally further comprises passing off-gas from a section of the urea production unit other than the finishing section, for example from the urea evaporation section, to the finishing treatment section. For example, at least part of a stream comprising water vapor evaporated in the urea evaporation section can be supplied to the finishing treatment section.

The process comprises combining aqueous ammonium nitrate solution and at least some urea liquid in a urea ammonium nitrate section (UAN production section) so as to obtain an aqueous solution of urea ammonium nitrate (UAN).

In the process of the invention, a part of the purified aqueous urea solution and/or concentrated urea liquid is combined with aqueous ammonium nitrate solution. Accordingly, the aqueous ammonium nitrate solution is combined with purified aqueous urea solution in case the process does not involve subjecting at least part of the purified aqueous urea solution to evaporation, and the aqueous ammonium nitrate solution is combined with purified aqueous urea solution and/or concentrated urea liquid if the process involves subjecting at least part of the purified aqueous urea solution to evaporation. However, this is not essential and that in principle urea supplied to the UAN production section can be obtained from any source.

In a preferred embodiment a stream of concentrated urea liquid supplied to the UAN production section comprises a minor part of the total amount of urea liquid supplied to the UAN production section. This allows for adjustment and control of the urea concentration in the UAN production section.

Optionally, a part of the purified aqueous urea solution obtained from the recovery section of the urea production unit can be supplied to the UAN production section, whereas another part can be supplied to the evaporation section and subsequently to the finishing section. Accordingly, the urea concentration of the urea liquid supplied to the UAN production section can for example be different from the urea concentration of urea liquid supplied to the finishing section.

The UAN production section preferably comprises a mixing unit, for instance comprises a static mixer or a pipe mixer, for example a series of static mixers. The process preferably comprises mixing aqueous ammonium nitrate solution and urea liquid.

The UAN products obtained with the present process contain for example 28 wt. % to 32 wt. % of total nitrogen and typically of from 29 wt. % to 38 wt. % urea and of from 36 wt. % to 48 wt. % of ammonium nitrate, with the remainder being water.

In the process of the invention, a urea production unit comprises a finishing section adapted to solidify urea liquid. Usually, the urea liquid is concentrated before being subjected to solidification. The finishing section is for example the finishing section of the urea production unit wherein aqueous urea solution and/or concentrated urea liquid are produced.

The process optionally comprises solidifying urea liquid in the finishing section.

The solidification in the finishing section results in ammonia-containing off gas (finishing off-gas). The solidification for example comprises prilling, granulation, and/or pastillation of urea in the finishing section. The solidification in the finishing section preferably comprises exposing concentrated urea liquid to an air stream so as to obtain solid urea particles. The use of such air stream results in finishing off-gas. Accordingly, the finishing section has a gas outlet in fluid communication with a gas inlet of a finishing treatment section adapted to subject ammonia-containing off-gas of the finishing section to treatment with an acidic scrubbing liquid.

This finishing section may for example be a prilling tower, granulation section, pelletizing section, or a section or equipment based on any other finishing technique. A granulation section may for example be a fluidized bed-granulation, or a drum granulation, or a pan-granulation, or any other similar granulation device. The main function of this finishing section is the conversion of a urea liquid, for example urea melt, into a stream of solidified particles. To transfer the urea from the liquid phase into the solid phase, the heat of crystallization has to be removed. Moreover, usually some sensible heat is removed from the solidified urea particles, in order to cool them to a temperature that is suitable for further processing and handling, including safe and comfortable storage and transport of this final product. The resulting total removal of heat in the finishing section is usually done by evaporation of water and/or by cooling with air. For water evaporation, the water enters the finishing section either as part of the urea liquid, or is sprayed as liquid water at an appropriate place in the finishing process. Usually most of the heat is removed by cooling with air. Usually an amount of air equal to 3-30 kg of air per kg of final solidified product is applied, preferably 3-10 kg. This is the typical off-gas of the finishing section.

In the finishing section the air comes into direct contact with the urea melt and with the solidified urea particles. This leads to contamination of the air with urea dust and ammonia. Depending on the nature of the finishing section (prilling/granulation, type of granulation, conditions selected in granulation), the amount of urea dust present in the air may vary widely, values in the range of 0.05% to 10% by weight (with respect to the final product flow) having been observed. For a finishing section based on granulation, the amount of dust more typically is in a range of from 2% to 8% by weight. Urea in the finishing off-gas is mainly present as urea dust comprising particles with a diameter less than 500 μm, with a large fraction of particles smaller than 10 μm, such as sub-micron particles. Generally, this dust is carried along by the air stream when the air stream leaves the finishing section as off-gas. This presence of urea dust in the finishing off-gas usually makes a treatment comprising urea dust removal desirable, either for environmental or for efficiency considerations, before the air can be vented into the atmosphere. The removal of urea dust is challenging per se, since the amounts of off-gas (mainly air) are enormous, whilst the concentration of urea dust is low. An example airstream is of the order of 750 000 $Nm^3/h$. A typical concentration of urea dust therein is about 2 wt. %. Further, part of the urea dust is of a submicron size. Satisfying current standards implies the need to remove a major part of this submicron dust.

The solidification process may also comprise pelletizing, for example as described in WO 2006/111331. In such process, urea-comprising particles are produced in a pelletizer, comprising a feeding device, a belt and a device to remove the formed pellets from the belt, by feeding a urea containing liquid stream to the feeding device from which droplets of the liquid are dosed to the belt, whereon the urea-containing droplets solidify and cool to a temperature of <55° C. The formed urea-containing particles are removed from the belt.

In the process of the invention, a finishing treatment section is involved having a gas inlet in fluid communication with a gas outlet of the finishing section, adapted to subject ammonia-containing off-gas of the finishing section (finishing off-gas) to treatment with an acidic scrubbing liquid. The treatment with an acidic scrubbing liquid results in removal of at least part of the urea dust and/or ammonia. Hence, the process may comprise scrubbing finishing off-gas. Scrubbing for example comprises adding scrubbing liquid into a gas stream, usually in counter-current flow.

The finishing treatment section comprises at least one scrubber for scrubbing with acidic scrubbing liquid. The finishing treatment section may comprise additional scrubbers for scrubbing with acidic scrubbing liquids or other liquids.

Suitable types of scrubbers include for example venturi scrubbers, packed bed scrubbers, impingement scrubbers, and sieve tray scrubbers. The process may comprise scrubbing finishing off-gas. Scrubbing for example comprises adding scrubbing liquid into a gas stream, usually in counter-current flow.

In a venturi scrubber the effluent gas is forced or drawn through a venturi tube having a narrow "throat" portion. As the air moves through the throat it is accelerated to a high velocity. A scrubbing liquid in the form of droplets, typically of water, is added to the venturi, usually at the throat, and enters the gas flow. The water droplets used are generally many orders of magnitude larger than the contaminant particles to be collected and, as a consequence, accelerate at a different rate through the venturi. The differential acceleration causes interactions between the water droplets and the contaminant particles, such that the contaminant particles are collected by the water droplets. The collection mechanisms involve, primarily, collisions between the particles and the droplets and diffusion of particles to the surface of the droplets. In either case, the particles are captured by the droplets. Depending on the size of the contaminant particles, one or the other of these mechanisms may predominate, with diffusion being the predominant collection mechanism for very small particles, and collision or interception being the predominant mechanism for larger particles. A venturi scrubber can also be efficient at collecting highly soluble gaseous compounds by diffusion. A detailed description of these scrubbing mechanisms is discussed in Chapter 9 of Air Pollution Control Theory, M. Crawford, (McGraw-Hill 1976).

The finishing treatment section may comprise a single venturi scrubber or a plurality of venturi scrubbers. Further, one or more venturi scrubbers can themselves comprises one or more venturi tubes.

A venturi scrubber usually comprises three sections: a converging section, a throat section, and a diverging section. The inlet gas stream enters the converging section and, as the area decreases, gas velocity increases. Liquid is introduced either at the throat or at the entrance to the converging section.

The inlet gas, forced to move at extremely high velocities in the small throat section, shears the liquid from its walls, producing an enormous number of very tiny droplets. Particle and gas removal occur in the throat section as the inlet gas stream mixes with a fog of tiny liquid droplets. The inlet stream then exits through the diverging section, where it is forced to slow down.

In case of a finishing treatment section comprising a scrubber, the treatment section may comprise sections for one or more pre-treatments or post-treatments. For instance, a venturi scrubbing method as described in WO 2015/002535 can be used. Such method comprises quenching off-gas to a temperature below about 45° C. and/or to a temperature decrease of at least 50° C., and subjecting the quenched off-gas to scrubbing using at least one venturi scrubber. Quenching comprises adding aqueous quenching liquid to a gas stream, preferably by spraying, more preferably using an atomization nozzle, such as through a jet nozzle, for example co-currently with the gas stream. Quenching generally provides a liquid saturation near equilibrium. Preferably the quenching stream has a temperature of below 45° C., more preferably below 40° C., most preferably below 35° C. The typical air temperature of the off-gas exiting a finishing section of a urea plant, such as in fluid bed granulation, is about 110° C. After quenching, the temperature is preferably below 45° C. Accordingly, the temperature of the gas stream is lowered by typically more than 50° C., preferably more than 60° C., and most preferably more than 65° C. Preferably, the liquid is sprayed in such a way and consistency that liquid droplets are formed that are so small that the droplets evaporate quickly and a liquid saturation in the vapor near equilibrium is reached within a short time, for example with a droplet size of less than 700 µm or less than 500 µm, or less than 100 µm.

In addition, a method such as described in WO 2015/072854 can be used. In such method, the gas stream is subjected to quenching in at least two stages in series, using an upstream quenching liquid and a downstream quenching liquid, with the terms upstream and downstream being defined with reference to the flowing direction of the gas stream, wherein soluble particulate matter dissolves in the aqueous quenching liquid and wherein the downstream quenching liquid has a lower concentration of dissolved said particulate matter than the upstream quenching liquid. WO 2015/002535 and WO 2015/072854 are herewith incorporated by reference. Such quenching may provide for condensation of water on particles to be removed, thereby increasing their particle size, such that they are better removed in a venturi scrubber.

In a preferred embodiment, the finishing treatment section comprises a plurality of venturi scrubbers, operated in parallel. Preferably, the finishing treatment section is so designed that these parallel venturi tubes can be operated independently of each other, i.e. the number of venturi tubes used at the same time, can be adapted during the process as desired.

A preferred venturi scrubber comprises a so-called MMV-section (micro-mist venturi). The MMV-section consists of multiple parallel venturis. In the MMV-section large quantities of liquid are sprayed in the throat of the venturis co-current with the gas-flow through single phase nozzles, creating a consistent and adjustable liquid droplet-size, typically in a range of from 50 µm to 700 µm. The liquid droplet size is one of the parameters that can be used to control the efficiency of dust-removal.

A preferred system is that provided by Envirocare, comprising a quenching section, and downstream thereof a MMV-section.

In a packed bed scrubber, separation is usually achieved by contact between the gas and the scrubbing liquid over a random packed bed. In an impingement scrubber, separation is usually achieved by inertia through a central impingement plate. For example, an off-gas stream enters the unit from the bottom and flows upward through a series of trays, each containing perforations. Scrubbing liquid is introduced from above the top tray and cascades downward to the lower trays. The gas stream passes through the perforations and accelerates. This results in a fluidized zone of liquid and gas. An impingement scrubbing unit is usually furnished with a final demister section. Yet a further option for the scrubber is a sieve tray scrubber. Herein, liquid gas contact occurs on the sieve tray. For example, a liquid stream flows horizontally while the gas passes through the sieves.

Yet a further option is a treatment section comprising a wet electrostatic precipitator (WESP). Wet electrostatic precipitators of this general type are known and described in prior art patents including U.S. Pat. Nos. 1,339,480; 2,722,283; 4,389,225; 4,194,888; 6,106,592; and the prior art discussed and cited therein.

The finishing treatment section preferably comprises two parts in series, a part for scrubbing with acidic scrubbing liquid and a urea dust removal part. The parts are optionally separate compartments. The dust removal part, such as a venturi scrubber, is preferably upstream (with respect to the off-gas stream) of the part for scrubbing with acidic scrubbing liquid.

In one embodiment, in addition to the AN plant, also a calcium ammonium nitrate plant is present. Calcium ammonium nitrate or CAN, also known as nitro-limestone, is a widely used inorganic fertilizer. One variety of calcium ammonium nitrate is made by adding powdered limestone/calcium carbonate to ammonium nitrate; another, fully water-soluble version, is a mixture of calcium nitrate and ammonium nitrate, which crystallizes as a hydrated double salt: $5Ca(NO3)2.NH4NO3.10H2O$. The finishing section of the CAN plant (in either process) produces a CAN off-gas, gas which can also be scrubbed in the finishing treatment section. The finishing treatment section wherein also the CAN off-gas is scrubbed, comprises 2 separate compartments in series for scrubbing with acidic scrubbing liquid, designed to allow the spent scrubbing liquids of each compartment to be used differently. Generally, the compartment for scrubbing CAN off-gas is positioned downstream of the compartment for scrubbing AN off-gas.

In the present invention, the scrubber may comprise an overflow of the acidic scrubber part. The acidic scrubbing is for removing ammonia.

As mentioned above, the utilized scrubbing liquid from the finishing treatment section, can be sent to the mixing unit for the UAN synthesis. In the event of the presence of a CAN plant, this will generally require first removing a calcium containing salt solution. In an interesting embodiment, said utilized scrubbing liquid can itself be used as a UAN product stream. Accordingly, the scrubbing liquid can be merged with a UAN product stream, or it can be stored in a tank for later use.

The finishing treatment section for example comprises a venturi scrubber or a WESP, more preferably a combination of, in series, a wet scrubber (such as a tray scrubber) and, a venturi scrubber, with the venturi scrubber more preferably downstream of the wet scrubber. More preferably, the venturi scrubber comprises a plurality of venturi tubes in parallel. In another preferred embodiment, a WESP is positioned downstream of the wet scrubber, or downstream of the Venturi scrubber, or most preferably in series after the wet scrubber and the Venturi scrubber. Optionally, the finishing treatment section comprises a scrubber for scrubbing with acidic scrubbing liquid downstream of the venturi scrubber and/or WESP.

The invention also provides as mentioned a method of modifying a plant, wherein the method comprises adding a connection for fluid communication between an outlet for acidic condensate of said condensation section, and an inlet of said finishing treatment section, such as piping or tubing.

The method is usually a method for modifying or revamping a pre-existing plant. The plant can be of various types and the method may comprise additional steps prior to adding said connection. The method may for example be a method for modifying a plant for producing urea ammonium nitrate and a solid urea product. The method may also be part of a method for modifying an ammonium nitrate plant, wherein the method further comprises adding a urea production unit and adding a UAN production section. The method may also be part of a method for modifying a plant for the production of UAN comprising a urea production unit, wherein the method further comprises expansion of the urea production unit by adding a finishing section. The method may also be part of a method for modifying a urea plant including a finishing section, wherein the method further comprises adding of a an ammonium nitrate section.

The invention also relates to a system for the production of at least urea and urea ammonium nitrate, comprising as mentioned (a) a urea production unit comprising a finishing section, (b) an ammonium nitrate section for producing ammonium nitrate in fluid communication (c) a urea ammonium nitrate section, and (d) a finishing treatment section having a gas inlet in fluid connection with said gas outlet for off-gas of said finishing section, adapted to subject ammonia-containing off-gas of the finishing section to treatment with an acidic scrubbing liquid, wherein said finishing treatment section comprises an inlet in fluid communication with said condensation section for receiving said acidic condensate.

Preferably, the inlet for receiving urea liquid of said urea ammonium nitrate section is in fluid connection with said urea production unit comprising a finishing section. Preferably, the urea production unit comprises a high pressure urea synthesis section comprising a high pressure stripper and a carbamate condenser and a urea reactor, or an integrated carbamate condenser and a urea reactor, wherein said urea production unit further comprises a recovery section and an evaporation section. Preferably, the ammonium nitrate section comprises an inlet in fluid communication for off-gas with one or more of said high pressure synthesis section, recovery section and evaporation section.

Preferably, the finishing treatment section comprises an outlet for a liquid stream in fluid communication with a point downstream of said outlet for ammonium nitrate solution, such as with an inlet of said mixing unit. Preferably, such system is also suitable for the production of a DEF product, wherein the urea production unit comprises a divider for dividing a stream of urea liquid in at least two streams, and a unit for adding an additive to one of said streams downstream of said divider and upstream of a finishing section, and a unit for preparing a DEF product from the other stream.

Preferably, the treatment section comprises a venturi scrubber, more preferably an MMV scrubber.

The drawing shows a process scheme for a non-limiting example of a process and system according to the invention. Nitric acid 1 and ammonia gas 2 are reacted to provide aqueous ammonium nitrate solution 3 in an ammonium nitrate section A, thereby also yielding AN off-gas 4. Aqueous ammonium nitrate solution 3 is supplied to urea ammonium nitrate section B and off-gas 4 from ammonium nitrate section A is supplied to condenser F. A part of the off-gas is condensed into acidic condensate 18, the non-condensed part 19 is vented. A part 20 of the acidic condensate is supplied to finishing treatment section C and used as acidic scrubbing liquid therein. Another part 21 of the acidic condensate is supplied to urea ammonium nitrate section B. In a urea production unit D urea is produced from carbon dioxide 5 and ammonia 6, yielding a urea liquid 9 (purified aqueous urea solution and/or concentrated urea liquid) which is supplied to finishing section E. Optionally, a part of the urea liquid 7 is supplied to urea ammonium nitrate section B. It is also possible that section B receives urea liquid from another urea production unit, instead of or in combination with urea liquid 7. In section B, urea liquid is mixed with aqueous ammonium nitrate solution 3 to provide UAN stream 8. The system also comprises finishing section E wherein concentrated urea liquid 9 from urea production unit D is solidified. Finishing section E yields a solid urea product 10 and is for example a granulator or prilling tower. Finishing section E uses drying/cooling air 11 and provides ammonia-containing off-gas 12 that is supplied to finishing treatment section C adapted to subject off-gas 12 to treatment with an acidic scrubbing liquid 13 to give a cleaned off-gas 14. Optionally, spent scrubbing liquid 15 is recycled by supplying it to urea ammonium nitrate section B. Optionally, off-gas from urea production unit D is supplied to finishing treatment section C as a stream 16 and/or to ammonium nitrate section A as stream 17.

The term "fluid communication" includes any connection any connection between a first part or section of a plant and a second part or section of a plant via which fluids, notably liquids, can flow from the first part of the plant to the second part of the plant. Such fluid communication is typically provided by piping systems, hoses, ducts, pumps, or other devices well-known to the skilled person for the transportation of fluids. The fluid communication can be direct fluid communication, such as any of the foregoing without involving any further equipment other than the fluid transportation devices themselves. The fluid communication can also be indirect, wherein the fluid may be transported via piping system, hoses, ducts or pumps, and also including other equipment such as strippers or reactors. As used herein, the terms "inlet" and "outlet" can also be used for intermediate streams.

The term "liquid stream" includes suspensions and dispersions and generally relates to a fluid stream comprising a continuous liquid phase. The term "gaseous stream" does not exclude the presence of entrained droplets and particles.

The invention claimed is:

1. A method for the production of urea ammonium nitrate comprising
   (a) subjecting ammonia and carbon dioxide to urea forming conditions so as to obtain an aqueous urea solution,
   (b) purifying the aqueous urea solution in a recovery section to remove residual ammonium carbamate so as to form a purified aqueous urea solution, and optionally subjecting at least part of the purified aqueous urea solution to evaporation so as to form concentrated urea liquid,
   (c) subjecting ammonia and nitric acid to ammonium nitrate forming conditions so as to form an aqueous ammonium nitrate solution;
   (d) combining said aqueous ammonium nitrate solution and at least a part of the purified aqueous urea solution and/or concentrated urea liquid in a urea ammonium nitrate section so as to obtain an aqueous solution of urea ammonium nitrate;
   (e) subjecting ammonia-containing off-gas resulting from the production of ammonium nitrate (AN off-gas) to condensation under acidic conditions so as to form an acidic condensate, and using at least part of the acidic condensate as an acidic scrubbing liquid in an off-gas treatment section downstream of a urea finishing section, said off-gas treatment section having a gas inlet in fluid communication with a gas outlet of said urea finishing section of a urea production unit, wherein the urea finishing section is adapted to solidify urea liquid, and wherein said off-gas treatment section is adapted to subject ammonia-containing off-gas of the urea finishing section to treatment with an acidic scrubbing liquid.

2. The method of claim 1, comprising recycling all or part of the scrubbing liquid utilized in the off-gas treatment section to the urea ammonium nitrate section.

3. The method of claim 1, comprising sending all or part of the scrubbing liquid utilized in the off-gas treatment section directly to the aqueous solution of urea ammonium nitrate.

4. The method of claim 2, wherein in addition a Diesel Exhaust Fluid (DEF) product is prepared, the method comprising dividing a stream of urea liquid of the urea production unit having the finishing section into at least two streams, adding an additive to one of said streams downstream of said dividing, and preparing a DEF product from the other stream, and wherein the stream with said additive is subjected to solidification in the finishing section.

5. The method of claim 1, wherein also the ammonia containing off-gas from the urea production unit and/or the urea ammonium nitrate section is sent to a gas inlet of the off-gas treatment section.

6. The method of claim 1, wherein ammonia-containing off-gas of the finishing section is subjected to scrubbing to remove droplets and particles and subsequently to scrubbing with acidic scrubbing liquid in said off-gas treatment section.

7. The method of claim 1, the method further comprising producing Calcium Ammonium Nitrate (CAN) granules by
   (f) subjecting a part of the aqueous ammonium nitrate solution of step (c) and a calcium salt stream, to a CAN finishing unit so as to form CAN-granules and a CAN off-gas, said CAN off-gas containing ammonia, ammonium nitrate and entrained Ca-containing particles;
   (g) feeding said CAN off-gas to the off-gas treatment section wherein said off-gas treatment section is adapted to treat said CAN off-gas with an acidic scrubbing liquid thereby forming a Ca-containing salt solution before recycling the scrubbing liquid to the UAN section.

8. A system for the production of at least urea and urea ammonium nitrate comprising:
   (a) a urea production unit comprising a urea finishing section, wherein the urea finishing section has a gas outlet for ammonia-containing off-gas,
   (b) an ammonium nitrate section for producing ammonium nitrate in fluid communication with a source of nitric acid and a source of ammonia, having an outlet for aqueous ammonium nitrate solution and an outlet for off-gas, and a condensation section in fluid communication with said outlet for off-gas, for condensing at least part of said off-gas to form an acidic condensate,
   (c) a urea ammonium nitrate section comprising a unit having an inlet in fluid connection with said outlet for aqueous ammonium nitrate solution and an inlet for receiving urea liquid, for combining said ammonium nitrate solution and said urea liquid, and having an outlet for urea ammonium nitrate solution, and
   (d) an off-gas treatment section downstream of a urea finishing section, having a gas inlet in fluid connection with said gas outlet for off-gas of said urea finishing section, adapted to subject ammonia-containing off-gas of the urea finishing section to treatment with an acidic scrubbing liquid,
   wherein said off-gas treatment section comprises an inlet in fluid communication with said condensation section for receiving said acidic condensate.

9. The system of claim 8, wherein said inlet for receiving urea liquid of said urea ammonium nitrate section is in fluid connection with said urea production unit comprising a finishing section
   wherein said urea production unit comprises a high pressure urea synthesis section comprising a high pressure stripper and a carbamate condenser and a urea reactor, or an integrated carbamate condenser and a urea reactor, wherein said urea production unit further comprises a recovery section and an evaporation section, and wherein said ammonium nitrate section comprises an inlet in fluid communication for off-gas with one or more of said high pressure synthesis section, recovery section and evaporation section.

10. The system of claim 8, wherein said off-gas treatment section comprises an outlet for a liquid stream in fluid communication with a point downstream of said outlet for aqueous ammonium nitrate solution.

11. The system of claim 10, which is adapted for the production of a DEF product, wherein the urea production unit comprises a divider for dividing a stream of urea liquid in at least two streams, and a unit for adding an additive to one of said streams downstream of said divider and upstream of a finishing section, and a unit for preparing a DEF product from the other stream.

12. The system of claim 8, wherein said off-gas treatment section comprises a venturi scrubber.

13. The system of claim 8, comprising a calcium ammonium nitrate (CAN) production section, said CAN production section comprising an inlet for ammonium nitrate in fluid communication with an outlet for ammonium nitrate from the ammonium nitrate section, wherein the CAN production section comprises a granulation section having an outlet for off-gas in fluid communication with a gas inlet of the off-gas treatment section.

14. The method of claim 4, wherein the additive is formaldehyde.

15. The system of claim 12, wherein said off-gas treatment section comprises a micro-mist venturi (MMV) scrubber.

16. The system of claim 8 which is adapted to perform a method comprising
   (a) subjecting ammonia and carbon dioxide to urea forming conditions so as to obtain an aqueous urea solution,
   (b) purifying the aqueous urea solution in a recovery section to remove residual ammonium carbamate so as to form a purified aqueous urea solution, and optionally subjecting at least part of the purified aqueous urea solution to evaporation so as to form concentrated urea liquid,
   (c) subjecting ammonia and nitric acid to ammonium nitrate forming conditions so as to form an aqueous ammonium nitrate solution;
   (d) combining said aqueous ammonium nitrate solution and at least a part of the purified aqueous urea solution and/or concentrated urea liquid in a urea ammonium nitrate section so as to obtain an aqueous solution of urea ammonium nitrate;
   (e) subjecting ammonia-containing off-gas resulting from the production of ammonium nitrate (AN off-gas) to condensation under acidic conditions so as to form an acidic condensate, and using at least part of the acidic condensate as an acidic scrubbing liquid in an off-gas treatment section having a gas inlet in fluid communication with a gas outlet of a finishing section of a urea production unit, wherein the finishing section is adapted to solidify urea liquid, and wherein said off-gas treatment section is adapted to subject ammonia-containing off-gas of the finishing section to treatment with an acidic scrubbing liquid.

17. The system of claim 10 wherein said point downstream of said outlet for aqueous ammonium nitrate solution is an inlet of the unit of the urea ammonium nitrate section.

18. The method of claim 7 wherein said calcium salt is calcium carbonate orcalcium nitrate.

* * * * *